(12) United States Patent
Ty

(10) Patent No.: US 11,969,350 B2
(45) Date of Patent: Apr. 30, 2024

(54) SPINAL IMPLANT WITH SURFACE PROJECTIONS

(71) Applicant: BEACON BIOMEDICAL, LLC, Jupiter, FL (US)

(72) Inventor: Dennis Ty, Jupiter, FL (US)

(73) Assignee: BEACON BIOMEDICAL, LLC, Jupiter, FL (US)

( * ) Notice: Subject to any disclaimer, the term of this patent is extended or adjusted under 35 U.S.C. 154(b) by 0 days.

(21) Appl. No.: 17/025,624

(22) Filed: Sep. 18, 2020

(65) Prior Publication Data

US 2021/0085470 A1 Mar. 25, 2021

Related U.S. Application Data

(60) Provisional application No. 62/903,283, filed on Sep. 20, 2019.

(51) Int. Cl.
| | |
|---|---|
| *A61F 2/44* | (2006.01) |
| *A61F 2/30* | (2006.01) |
| *A61F 2/46* | (2006.01) |

(52) U.S. Cl.
CPC .......... *A61F 2/30771* (2013.01); *A61F 2/442* (2013.01); *A61F 2/447* (2013.01); *A61F 2/4611* (2013.01); *A61F 2002/30593* (2013.01); *A61F 2002/30784* (2013.01); *A61F 2002/30891* (2013.01); *A61F 2310/00023* (2013.01)

(58) Field of Classification Search
CPC ...... A61F 2/30771; A61F 2/442; A61F 2/447; A61F 2/4611; A61F 2/30767; A61F 2002/30593; A61F 2002/30784; A61F 2002/30891; A61F 2310/00023

USPC ........................................... 623/17.11–17.16
See application file for complete search history.

(56) References Cited

U.S. PATENT DOCUMENTS

| | | | |
|---|---|---|---|
| 9,125,756 B2* | 9/2015 | Ullrich, Jr. | ............... C23C 14/34 |
| D907,771 S * | 1/2021 | Trudeau | ........................ D24/155 |
| 11,179,247 B2* | 11/2021 | Jebsen | .................... A61F 2/447 |
| 2005/0112397 A1* | 5/2005 | Rolfe | ..................... A61F 2/4455 |
| | | | 606/76 |
| 2005/0177238 A1* | 8/2005 | Khandkar | ........... A61L 27/3856 |
| | | | 623/23.57 |

(Continued)

FOREIGN PATENT DOCUMENTS

| | | |
|---|---|---|
| CN | 106510904 | 6/2018 |
| CN | 108670507 | 10/2018 |

(Continued)

*Primary Examiner* — Jessica Weiss
(74) *Attorney, Agent, or Firm* — Mchale & Slavin, P.A.

(57) ABSTRACT

An interbody spacer for use in spinal procedures. The interbody spacer has one or more surfaces with a unique surface pattern. The interbody spacer is preferably designed for use as an intervertebral spacer in spinal fusion surgery, where portions of an affected disc are removed from between two adjacent vertebrae and replaced with an interbody spacer that provides segmental stability, may correct a deformity, and allows for bone to grow between the two vertebrae to bridge the gap created by disk removal. The interbody spacer has one or more unique surfaces designed to aid in bone growth and attachment. The unique surface comprises one or more surface projections, referred to generally as surface projection pattern or matrix, which can be arranged to form unique patterns and structures.

7 Claims, 20 Drawing Sheets

(56) References Cited

U.S. PATENT DOCUMENTS

| | | | |
|---|---|---|---|
| 2010/0161061 A1* | 6/2010 | Hunt | A61B 17/1604 623/16.11 |
| 2010/0168798 A1* | 7/2010 | Clineff | A61C 8/0012 606/279 |
| 2013/0325142 A1 | 12/2013 | Hunter et al. | |
| 2015/0018956 A1* | 1/2015 | Steinmann | A61F 2/34 419/53 |
| 2016/0184103 A1 | 6/2016 | Fonte et al. | |
| 2018/0104063 A1* | 4/2018 | Asaad | A61F 2/447 |
| 2018/0110624 A1* | 4/2018 | Arnone | A61F 2/30767 |
| 2018/0193152 A1* | 7/2018 | Bauer | A61F 2/34 |
| 2019/0117410 A1* | 4/2019 | Parry | A61F 2/447 |
| 2019/0133783 A1* | 5/2019 | Unger | A61F 2/30771 |
| 2019/0159818 A1* | 5/2019 | Schneider | A61B 17/84 |
| 2019/0343648 A1* | 11/2019 | Ryan | A61F 2/30771 |
| 2019/0343652 A1* | 11/2019 | Petersheim | A61F 2/4611 |

FOREIGN PATENT DOCUMENTS

| | | |
|---|---|---|
| EP | 0561263 | 9/1993 |
| EP | 1961433 | 8/2008 |
| WO | WO2009034429 | 3/2009 |
| WO | WO2011022550 | 2/2011 |
| WO | WO 2011/060312 A2 * | 5/2011 |
| WO | WO2017106780 | 6/2017 |

\* cited by examiner

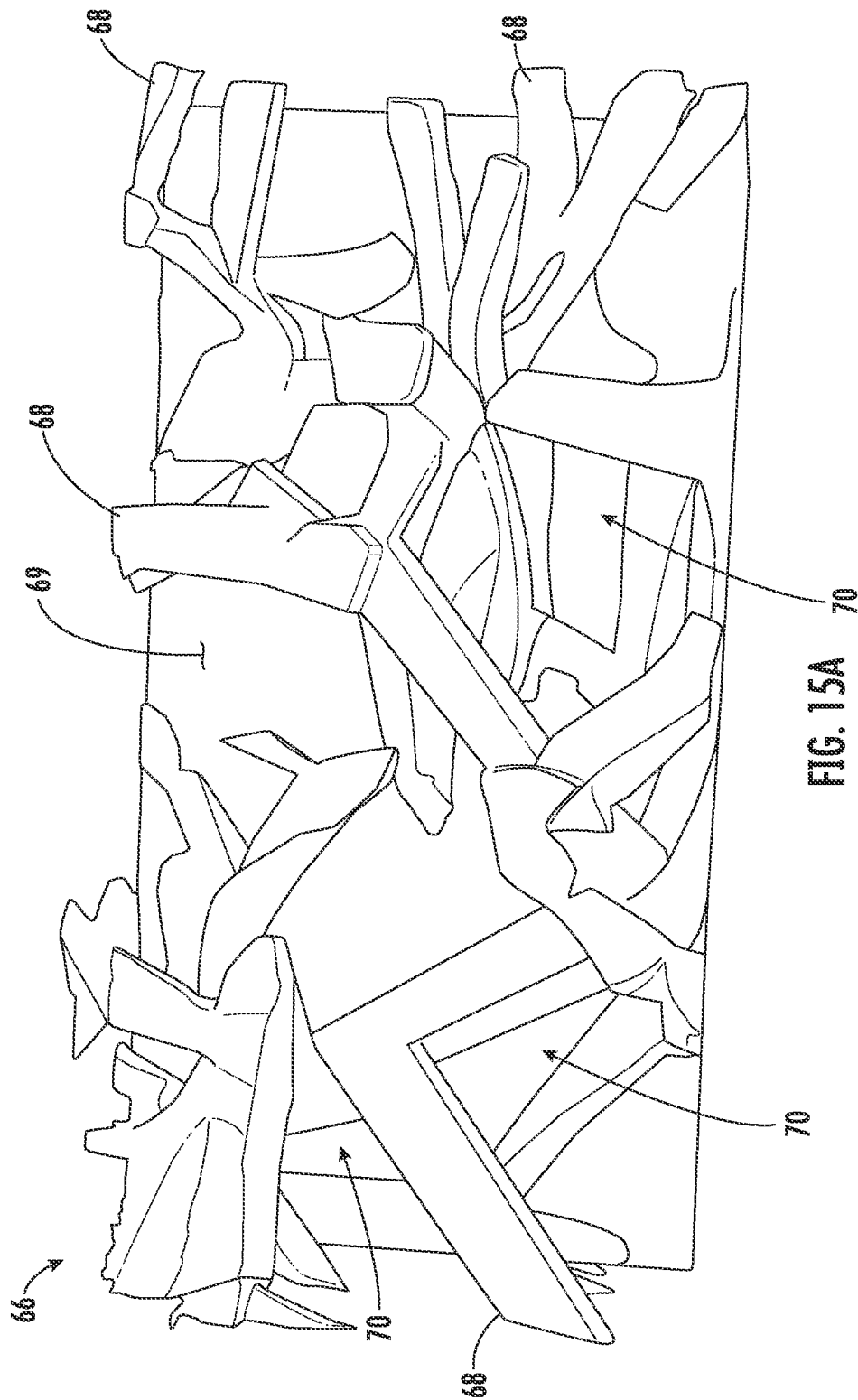

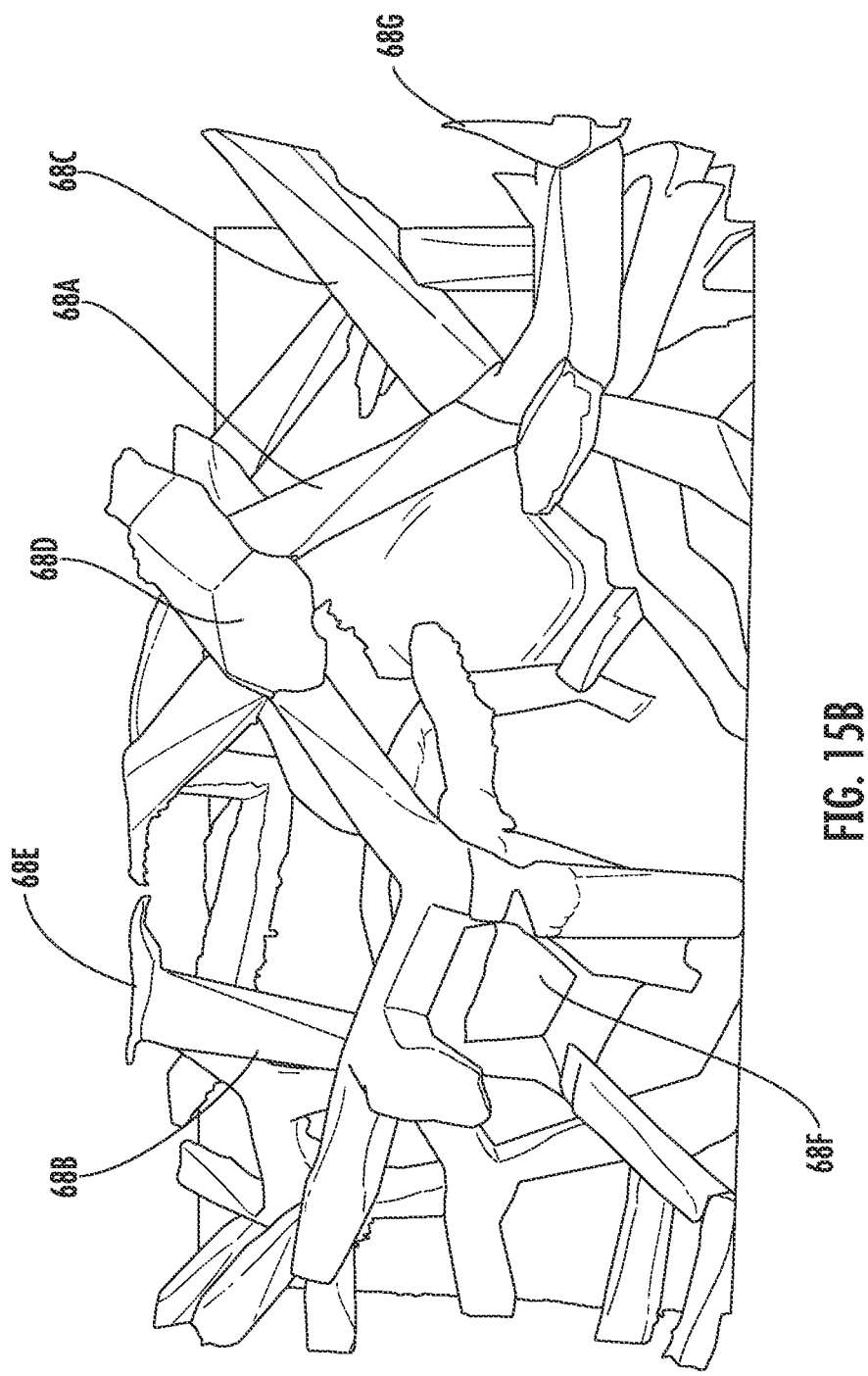

SPINAL IMPLANT WITH SURFACE PROJECTIONS

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 62/903,283, entitled "SPINAL IMPLANT WITH SURFACE PROJECTIONS", filed Sep. 20, 2019. The contents of the above referenced application are incorporated herein by reference in its entirety.

FIELD OF THE INVENTION

The present invention relates to bone fixation devices and procedures for the placement of these devices in an individual. More particularly, the present invention relates to a device for use in spinal fusion having surface projections, and to a unique surface for use in surgical procedures.

BACKGROUND OF THE INVENTION

Medical procedures often require the use of surgical hardware. In spine related surgeries, a common type of surgical hardware used by surgeons is a cage implant. Typical cage implants are porous and made of strong plastic or titanium, and are inserted into various portions or anatomical features of the spine, including in the cervical, thoracic, lumbar, sacroiliac joints, and facets. For example, the degeneration of the intervertebral disk, in particular, the degeneration of the nucleus pulposus, results in a loss of height in the affected disk space which is associated with a weakening of the annulus fibrosus and of the ligaments. As a consequence, the spinal column becomes instable and is more susceptible to horizontal displacement of the vertebral bodies with respect to one another. This horizontal movement of vertebral bodies results in impairments of the nerve roots in this region and/or of the spinal marrow, with pain resulting therefrom.

The principle treatment of these symptoms consists of the surgical removal of the nucleus pulposus and the insertion of support bodies in order to restore the normal height of the disk space. While there are a number of traditional systems and methods for inserting support bodies, there are a variety of demands on both the surgeon performing an intervertebral disk procedure and on the spinal spacers themselves.

A Transforaminal Lumbar Interbody Fusion (TLIF) is a surgical procedure that uses a posterior and lateral approach to access the disc space and insert a spacer. To gain access to the disc space, typically, a facet joint is removed and access is gained via the nerve foramen. While more technically demanding of the surgeon than other fusion techniques, a TLIF offers a number of clinical advantages.

When compared to a Posterolateral Fusion (PLF), a TLIF approach leaves much more of the soft tissue intact, which is less traumatic for the patient. Further, a PLF does not provide access to the disc space.

While a Posterolateral Interbody Fusion (PLIF) provides access to the disc space, a TLIF approach also provides access to the interbody space, but without the need for manipulation of neural elements, reducing the risk of postoperative neural deficit. Additionally, in a TLIF, only a single spacer is placed. More specifically, the TLIF spacer is placed in the anterior aspect of the disc space, thus providing space for a substantial fusion mass in the posterior aspect of the disc space where the natural compression occurs.

However, traditional TLIF procedures do suffer from a number of shortcomings. For example, traditional interbody spacers are coupled to an inserter by stationary threads formed in the body of the interbody spacer. Furthermore, in order to place the desired spacer in the anterior aspect of the disc space from an oblique posterior approach, traditional procedures demand that the spacer be released from the inserter and then tamped into place. The two-step insertion of this spacer is generally recognized among surgeons as cumbersome and may cause unneeded damage to bone and tissue, thereby increasing patient discomfort and increasing the amount of time sufficient to complete healing.

SUMMARY OF THE INVENTION

The present invention is directed towards a device, preferably an interbody spacer for use in spinal procedures, having one or more surfaces with a unique surface pattern designed to aid in bone growth and attachment. The present invention is also directed towards a unique surface with a unique surface pattern which can be used in spinal procedures to aid in bone growth and attachment. The interbody spacer is preferably designed for use as an intervertebral spacer in spinal fusion surgery, where portions of an affected disc are removed from between two adjacent vertebrae and replaced with an interbody spacer that provides segmental stability, may correct a deformity, and allows for bone to grow between the two vertebrae to bridge the gap created by disk removal. The interbody spacer has one or more unique surfaces designed to aid in bone growth and attachment. The unique surface comprises one or more surface projections, referred to generally as surface projection patterns or matrixes, which can be arranged to form unique patterns and structures.

Accordingly, it is an objective of the invention to provide a unique interbody spacer configured to aid in bone growth and attachment.

It is a further objective of the invention to provide for an interbody spacer having one or more unique surfaces designed to aid in bone growth and attachment.

It is yet another objective of the invention to provide for an interbody spacer having one or more unique surfaces comprising a surface projection pattern or matrix designed to aid in bone growth and attachment.

It is a further objective of the invention to provide a unique surface configuration designed to aid in bone growth and attachment.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 15A is a top view of the portion of the surface of the interbody spacer shown in FIG. 11;

FIG. 15B is an alternative top view of the surface of the interbody spacer illustrated in FIG. 15A;

DETAILED DESCRIPTION OF THE INVENTION

Figure 1:
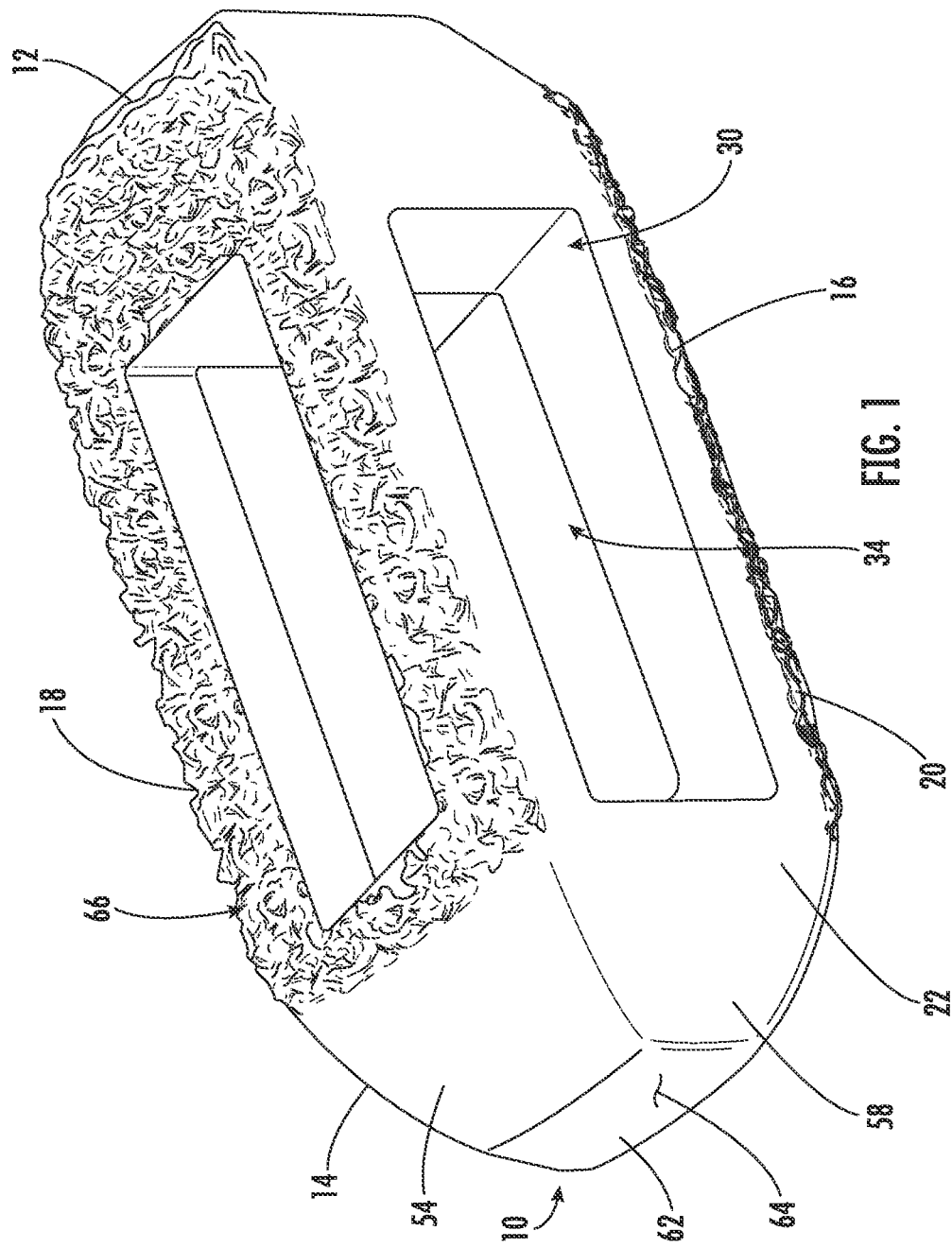
FIG. 1 is a front side perspective view of an illustrative embodiment of an interbody spacer having a surface designed to aid in bone growth and attachment.
Figure 2:
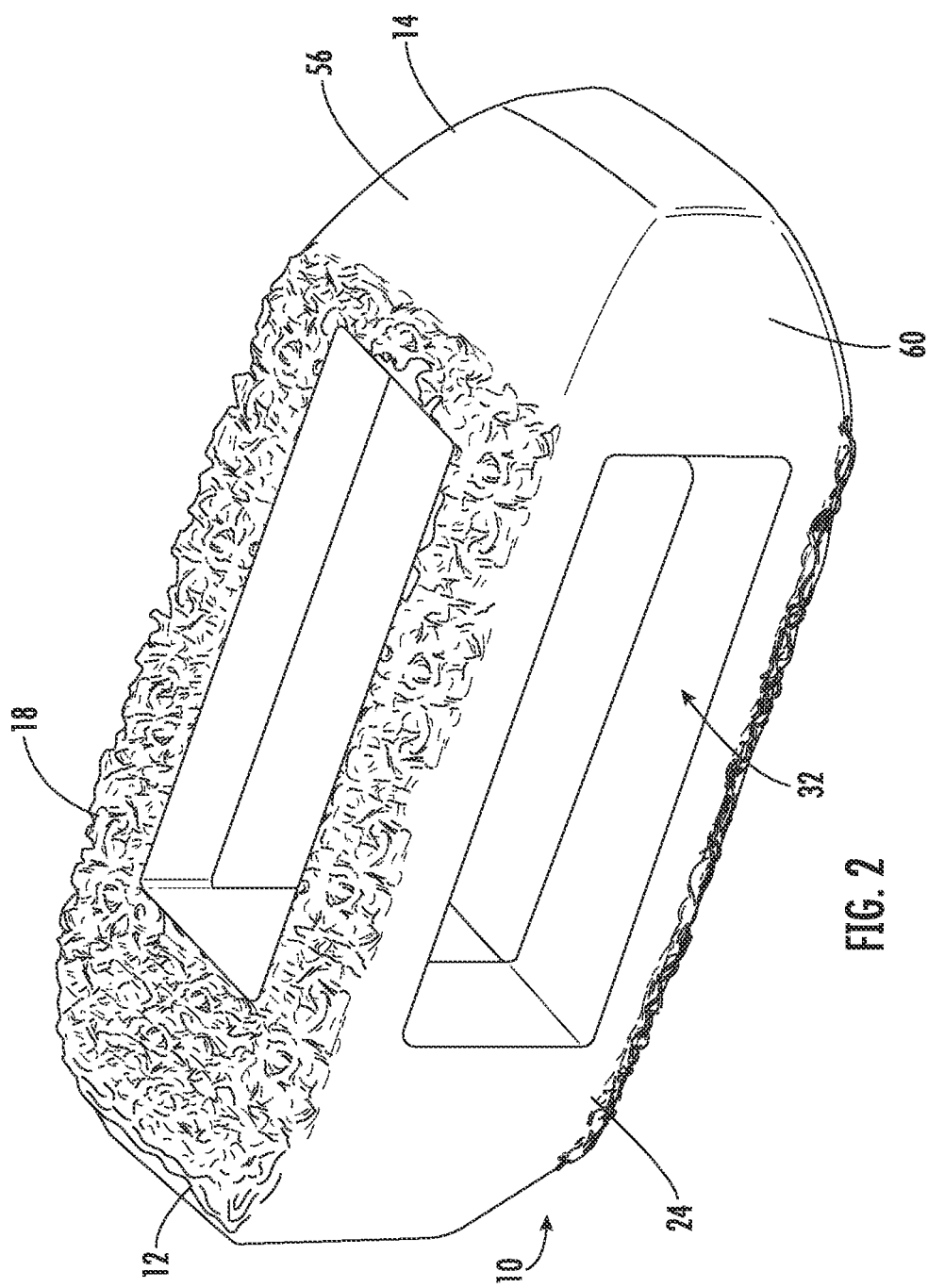
FIG. 2 is an alternative front side perspective view of the interbody spacer.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-10, an illustrative embodiment of an interbody spacer, referred to generally as interbody spacer 10, having one or more surfaces with a unique surface pattern, is shown. The interbody spacer 10 is preferably designed for use as an intervertebral spacer in spinal fusion surgery, where portions of an affected disc are removed from between two adjacent vertebrae 102 and 104 (see FIG. 16) and replaced with an interbody spacer 10 that provides segmental stability, may correct a deformity, and allows for bone to grow between the two vertebrae to bridge the gap created by disk removal. Preferably, the interbody spacer 10 is constructed from titanium, preferably medical grade titanium. However, the interbody spacer 10 may be made of any material known to one of skill in the art, preferably of a material useful for its intended purpose. Although the interbody spacer 10 may be manufactured in a manner known to one of skill in the art, a titanium grade interbody spacer 10 may be constructed using a three-dimensional (3D) printing technique, such as a 3D titanium printing technique using a powder bed metal 3D printer and a process such as direct metal laser sintering (DMLS). In this process, the interbody spacer 10 is built using a layer by layer approach, with a laser, typically a carbon dioxide laser, which melts the powder and fuses the titanium together.

As illustrated, the interbody spacer 10 assumes a generally rectangular shape having a proximal end 12 that will be closest to a surgeon during use, a distal end 14 that will likely be the leading edge of insertion during use, and a main body 16 therebetween. In general, the proximal end 12 is constructed and arranged for connection to an insertion tool that allows the interbody spacer to be grasped or locked into a specific orientation with respect to the insertion tool. The distal end 14 is constructed to aid in insertion of the interbody spacer 10 in between, for example, adjacent vertebrae 102 and 104.

The main body 16 comprises a first or upper wall or surface 18, a second or lower wall or surface 20, and two opposing side walls 22 and 24. The first upper wall or surface 18 comprises an opening, illustrated as an upper surface slotted opening 26, see FIG. 3. The second lower wall or surface 20 comprises an opening, illustrated as a lower surface slotted opening 28, see FIG. 9. Side wall 22 comprises an opening, illustrated as a first side wall slotted opening 30, see FIG. 1. Side wall 24 comprises an opening, illustrated as a second side wall slotted opening 32, see FIG. 2. While each of the openings 26, 28, 30, and 32 are shown having a particular shape and size, i.e. greater than 50% of the surface area, each opening 26, 28, 30, and 32 may be configured to assume any shape or size, so that the diameter, width or length of any one of openings 26, 28, 30, and 32 is larger or smaller than illustrated. Openings 26, 28, 30, and 32 expose an internal cavity 34. The interbody spacer internal cavity 34 is configured to hold bone growth material packed inside. While the interbody spacer internal cavity 34 is shown to provide a completely open or hollow space, the hollow or empty space can be constructed to assume any size or shape.

Figure 3:
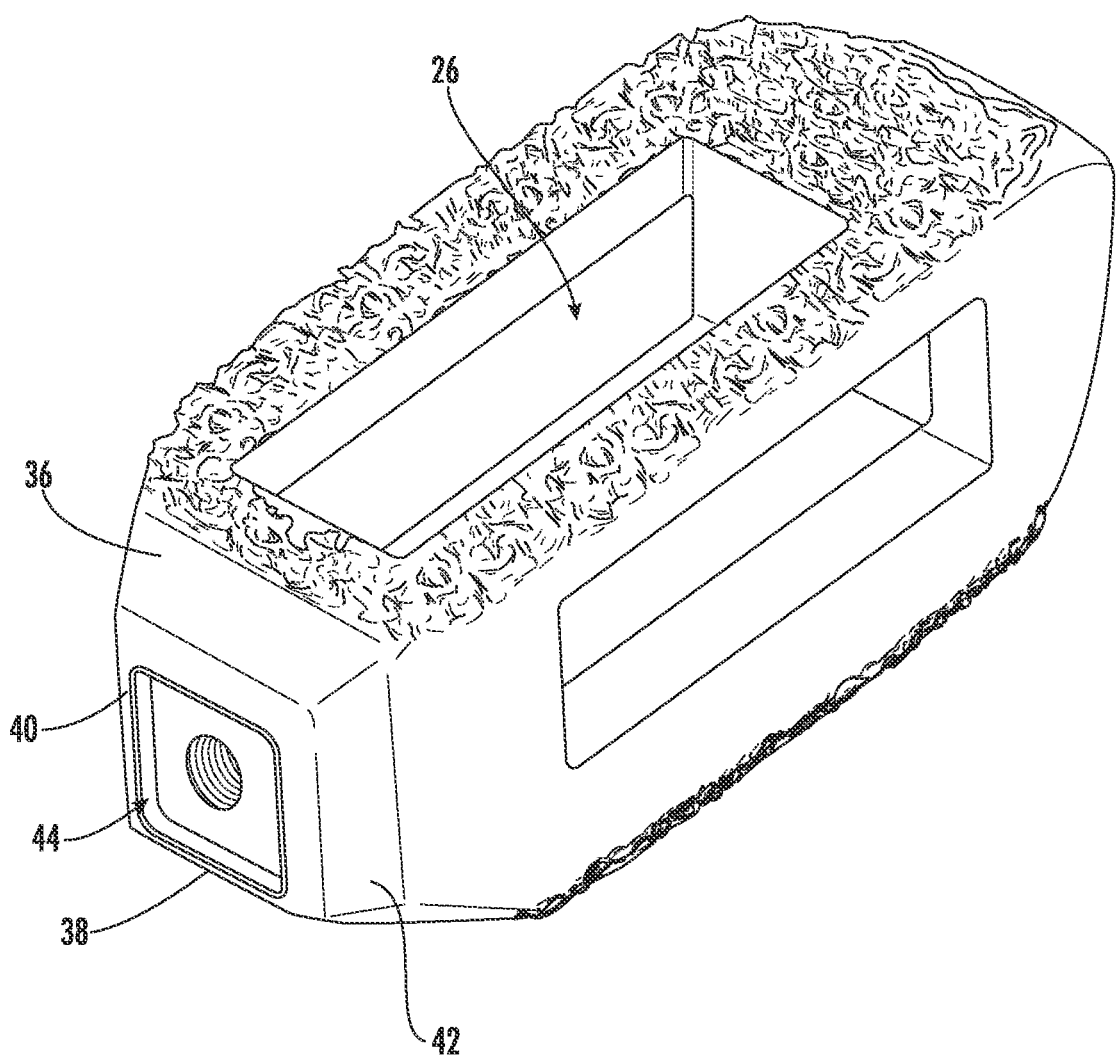
FIG. 3 is a back-side perspective view of an illustrative embodiment of the interbody spacer.
Figure 4:
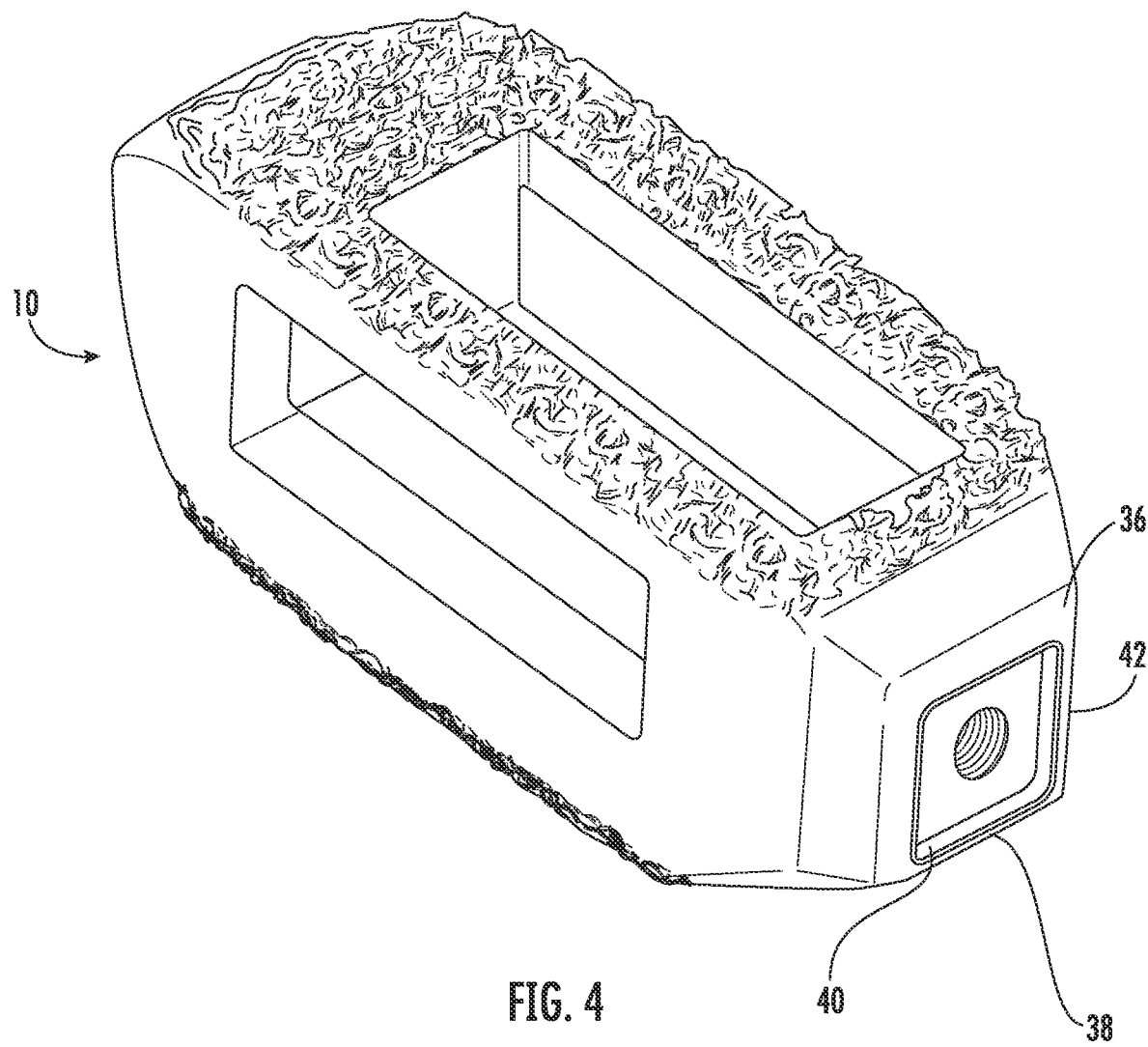
FIG. 4 is an alternative back-side perspective view of the interbody spacer.
Figure 5:
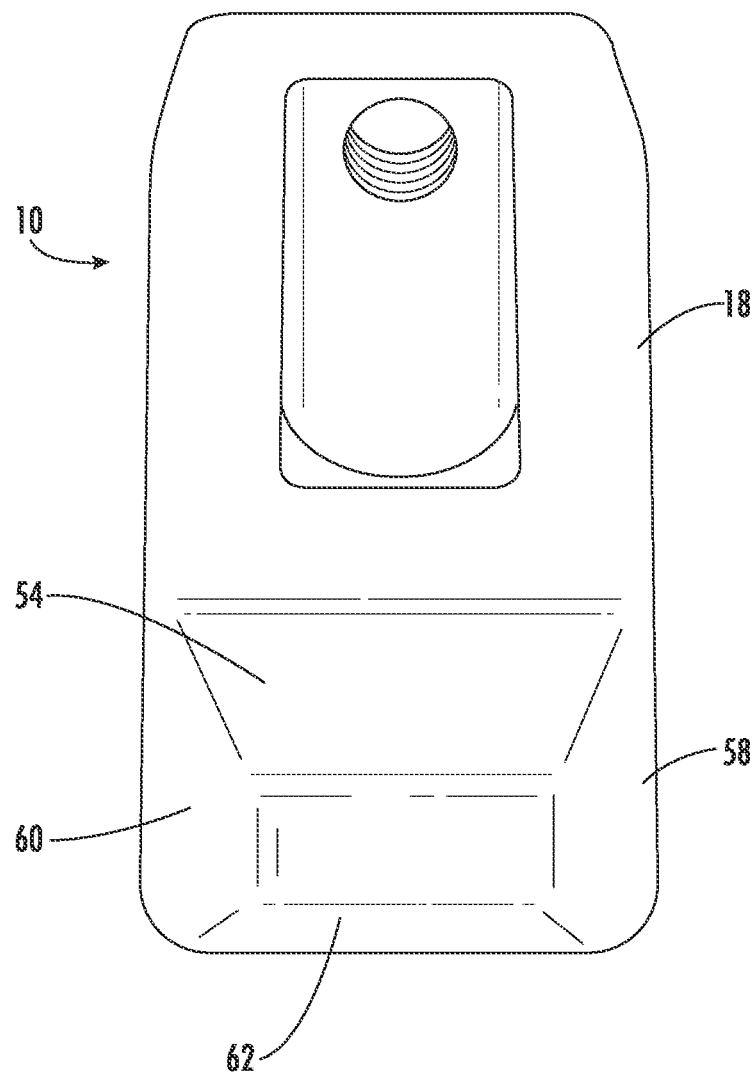
FIG. 5 is a front view of the interbody spacer.
Figure 6:
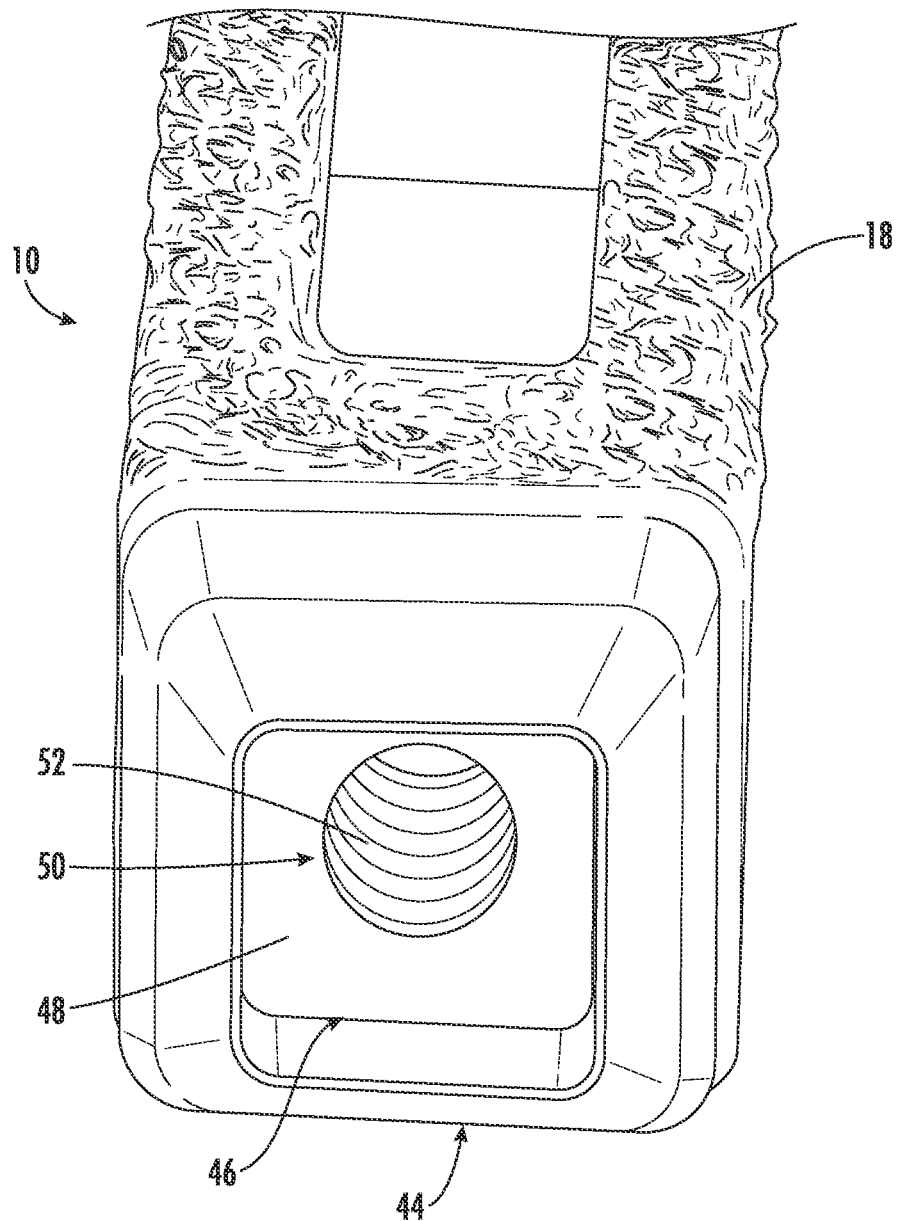
FIG. 6 is a back view of the interbody spacer.
Figure 7:
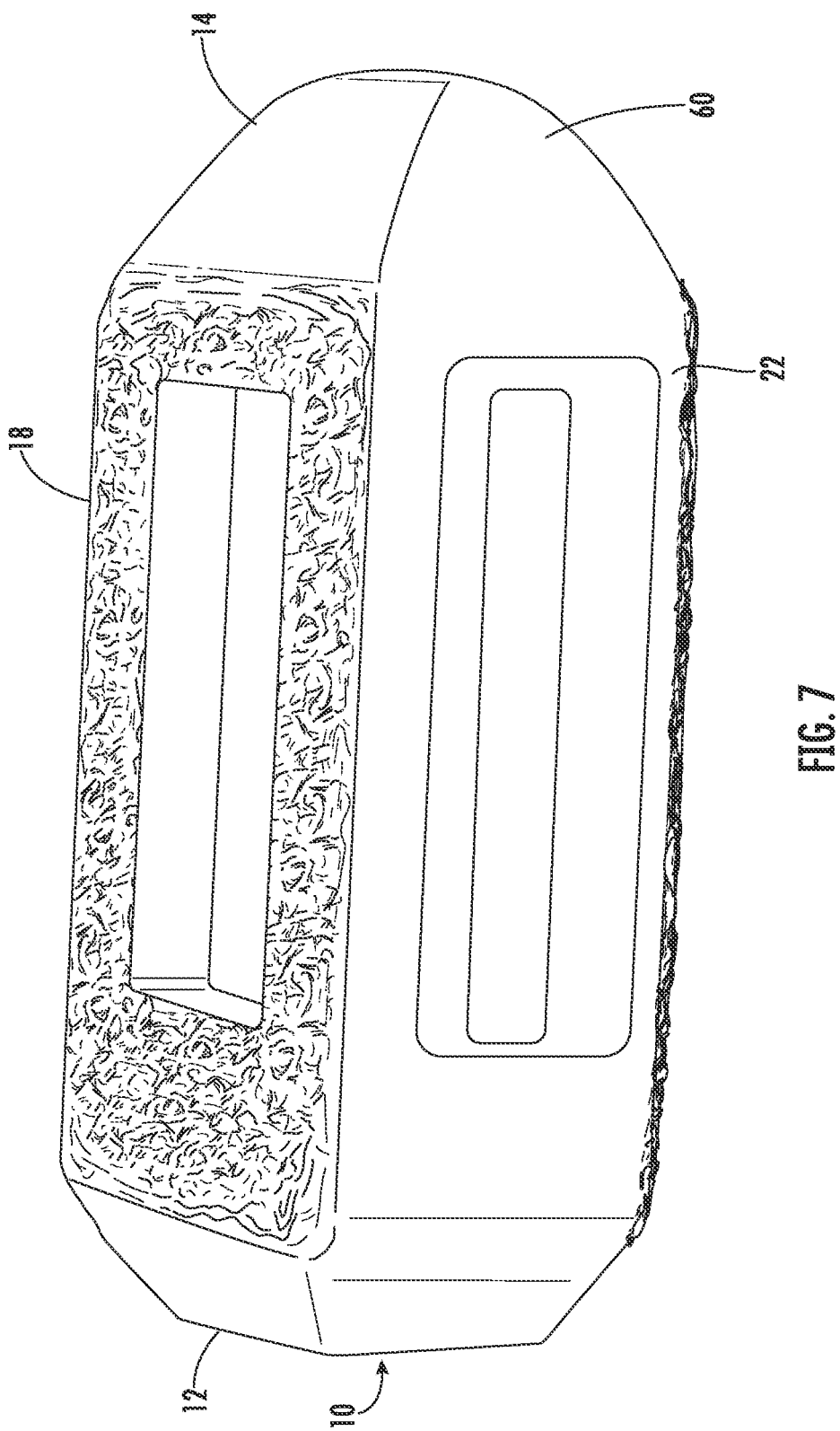
FIG. 7 is a right-side view of the interbody spacer.
Figure 8:
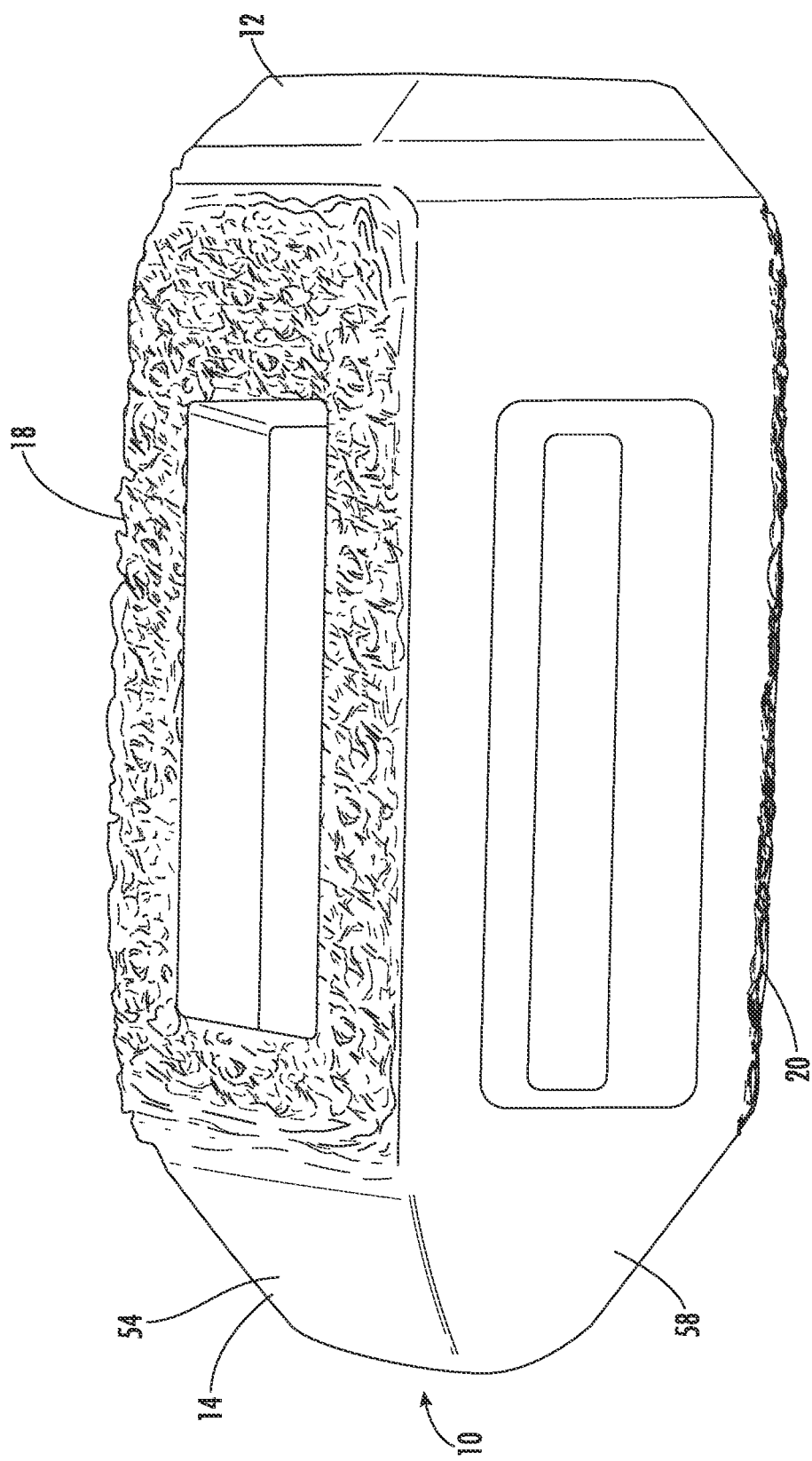
FIG. 8 is a left-side view of the interbody spacer.
Figure 9:
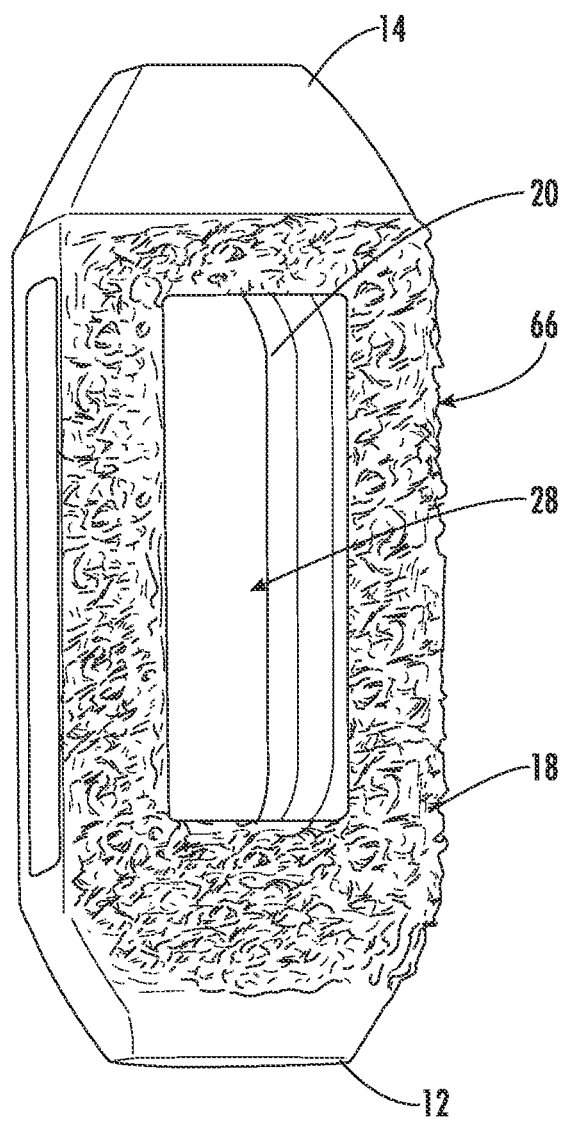
FIG. 9 is a top view of the interbody spacer.
Figure 10:
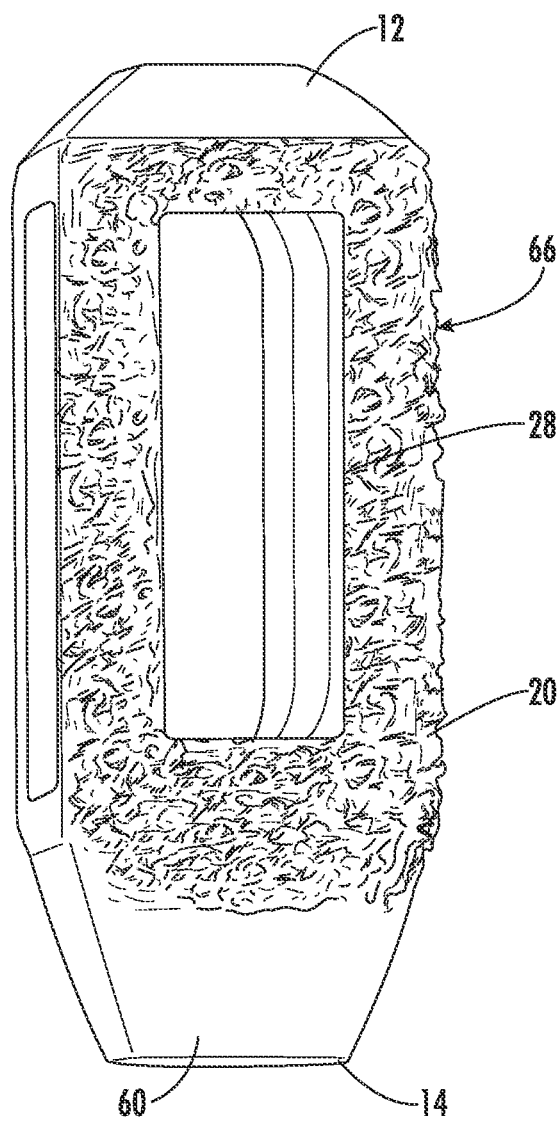
FIG. 10 is a bottom view of the interbody spacer.
Figure 11:
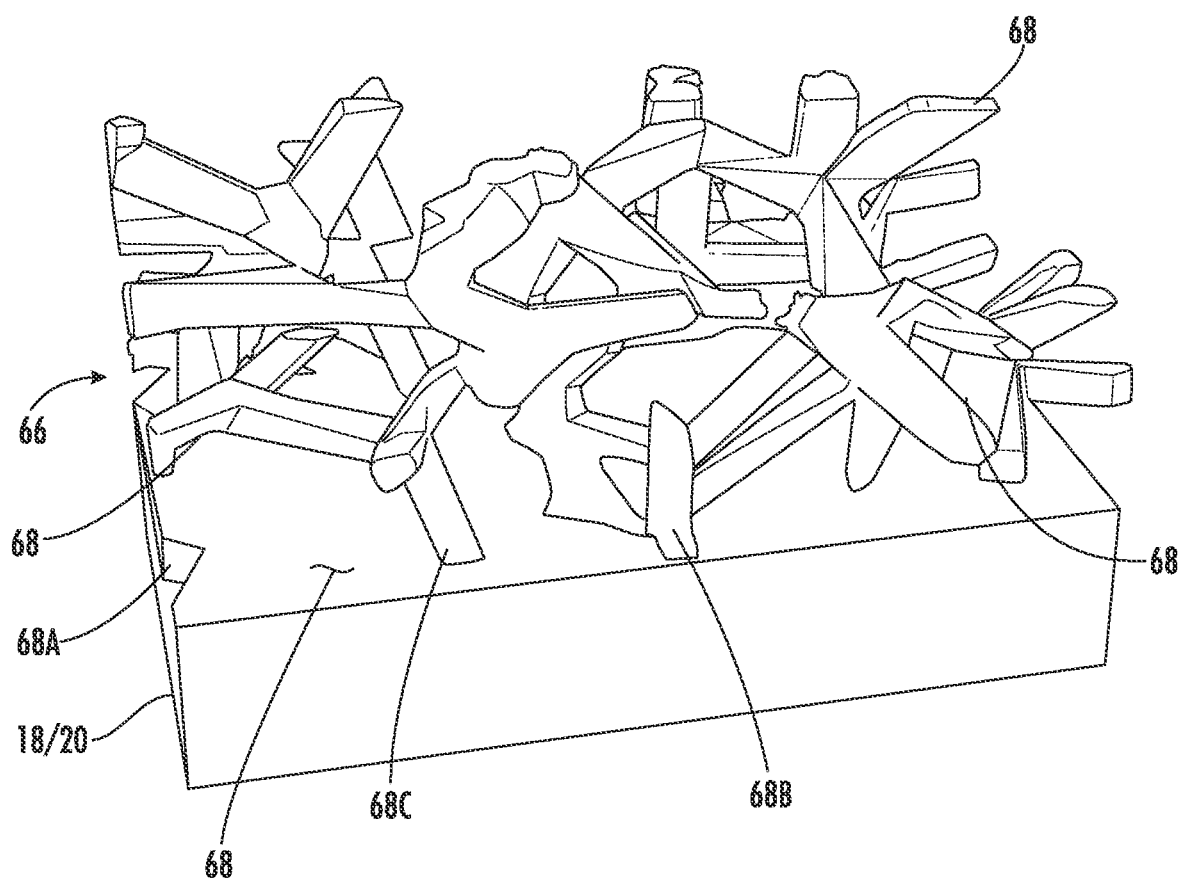
FIG. 11 is an enlarged, perspective view of a portion of a surface of the interbody spacer.
Figure 12:
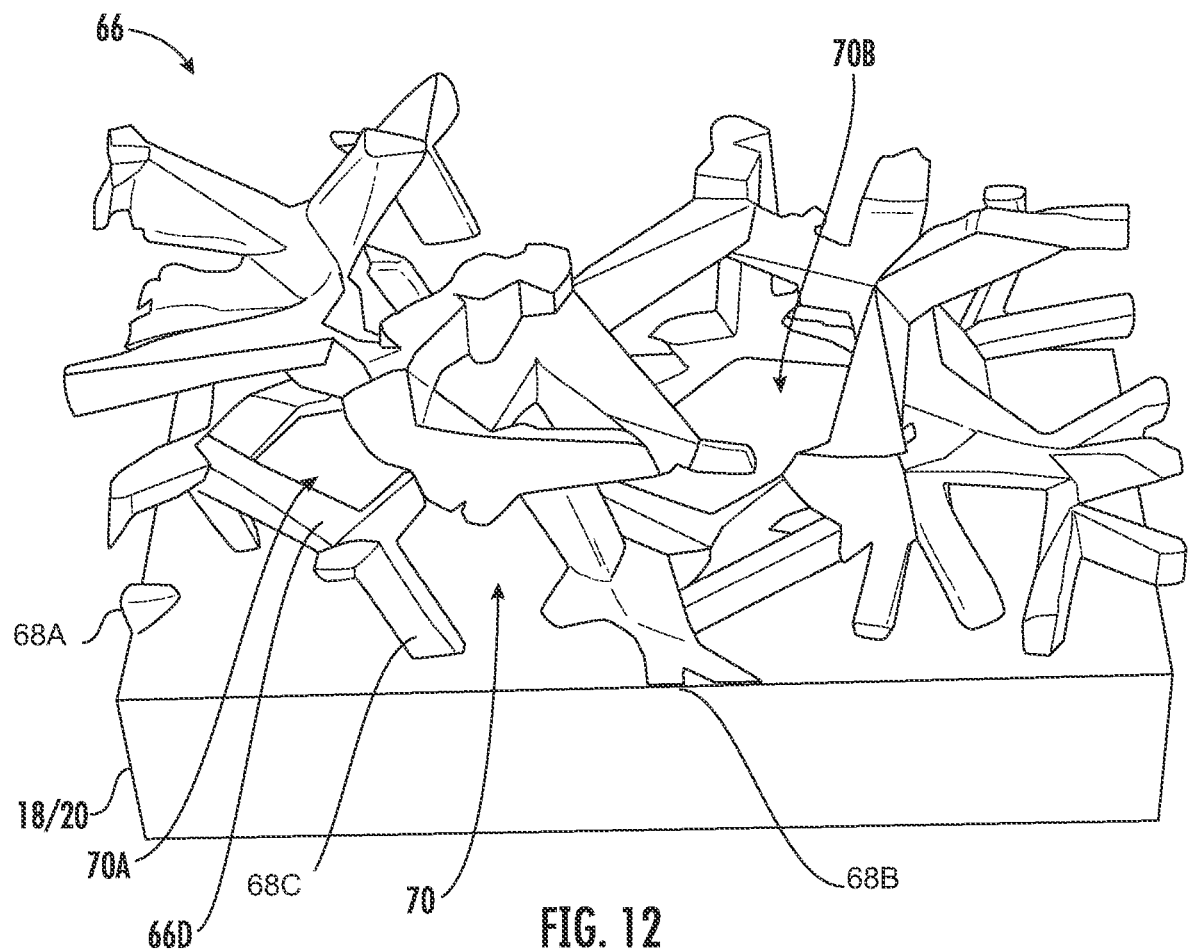
FIG. 12 is a front view of the portion of the surface of the interbody spacer shown in FIG. 11.

The proximal end 12 of the interbody spacer 10 is preferably constructed and arranged for connection to an insertion tool that allows the interbody spacer 10 to be grasped or locked into a specific orientation with respect to the insertion tool. As illustrated in FIGS. 3 and 4, the proximal end 12 may be configured to contain a tapered end, with side walls 36, 38, 40, and 42 having angled or sloping (sloping towards the internal cavity 34) surfaces. The side walls 36, 38, 40, and 42 terminate in an opening 44, thus forming an insertion tool receiving recessed cavity 46, see FIG. 6. Formed with a wall or solid surface 48 is a secondary opening, referred to generally as an insertion tool engaging opening 50 which is designed to receive and be secured with at least a portion of an insertion tool. The insertion tool engaging opening 50 is shown with female threading 52 configured to engage or cooperate with corresponding male threading associated with an insertion tool. While illustrated with threading, other mechanisms for securing, cooperating, or mating with an insertion tool known to one of skill in the art may be used.

The distal end 14 is preferably constructed to aid in insertion of the interbody spacer 10. The distal end 14 may comprise of a plurality of angled surfaces, 54, 56, 58, and 60, each ending to form a tapered interbody spacer end insertion point 62. The tapered interbody spacer end insertion point 62 is shown having a generally planar or flat surface 64.

The first or upper wall, or surface 18, and the second or lower wall, or surface 20, each comprise a unique surface covered with or having one or more surface projections, referred to generally as a surface projection pattern or matrix (also referred to as a surface scaffold 66) when arranged together to form a unique pattern or matrix. While the upper surface 18 is shown having the entire surface covered with surface projection pattern/matrix or scaffold 66, the upper surface 18 may be configured to comprise less than the entire surface being covered by the surface projection pattern/matrix or scaffold 66. While the lower surface 20 is shown having the entire surface covered with surface projection pattern/matrix or scaffold 66, the lower surface 20 may be configured to comprise less than the entire surface being covered by the surface projection pattern/matrix or scaffold 66.

Referring to FIGS. 11-15B, an illustrative embodiment of a representation of the surface projection pattern or matrix 66 is shown. The surface projection pattern or matrix 66 comprises a plurality of linear segments 68 (also referred to as surface projection 68) which extend upwardly from surface 69. While the embodiment described illustrates linear segments, other shapes such as rounded segments, curved segments, or multiple linear segments connected together to form a non-linear length or overall shape, may be used as well. Such use may be independent of or in combination with the linear segments. The linear segments 68 are preferably irregularly shaped, but may be constructed to be uniform in shape. The irregular shape single linear segment 68 may, for example, have an elongated body that has a curvature or twisting along a longitudinal axis which may cause the body to have a flat surface or section along one side, for example, linear segments 68A, 68B, or 68C, see FIG. 15B. The linear segment 68 may terminate in an irregular shaped flat end, see 68D, 68E or 68F, or a pointed, slanted end, see 68C or 68G. The linear segments 68 may be arranged as a single unit, see for example 68A, as part of a group having several linear segments extending from a single focus point or area, see 68B, a single linear segment which branches off into several additional linear segments, 68C, or combinations thereof.

If a single linear segment comprises branches, the branching might result in single branch, multiple branches, sub-branching in which one or more linear segments 66 of a branched segment may form additional branching, or combinations thereof. Any of the branched segments may be oriented in any direction, and orientated above or below other branched segments. The linear segments 68, whether as a single unit, part of a group having several linear segments extending from a single focus point or area, or as a single linear segment with one or more branches, are preferably arranged to form a complex pattern or matrix that forms pores 70, defined as openings or channels between one or more linear segments 68. The surface projection pattern or matrix 66 formed to comprise one or more pores 70 may also be defined as a porous scaffold. Preferably, the pores 70 formed in the porous scaffold are open pores, i.e. pores 70 that are connected to each other through various channels, such as voids 71A or interstices, 71B, see FIG. 13. Alternatively, or in addition to, the surface projection pattern or matrix porous scaffold 66 may comprise closed pores, i.e. pores surrounded by pore walls and disconnected from each other. Depending on the arrangement, the pores 70 may be defined by linear segments 68 which are joined together or in close proximity to form a pore, see for example, 70A, FIG. 12. The pores 70 may also be defined by non-congruent shape or space defined by two or more linear segments 68.

Figure 13:
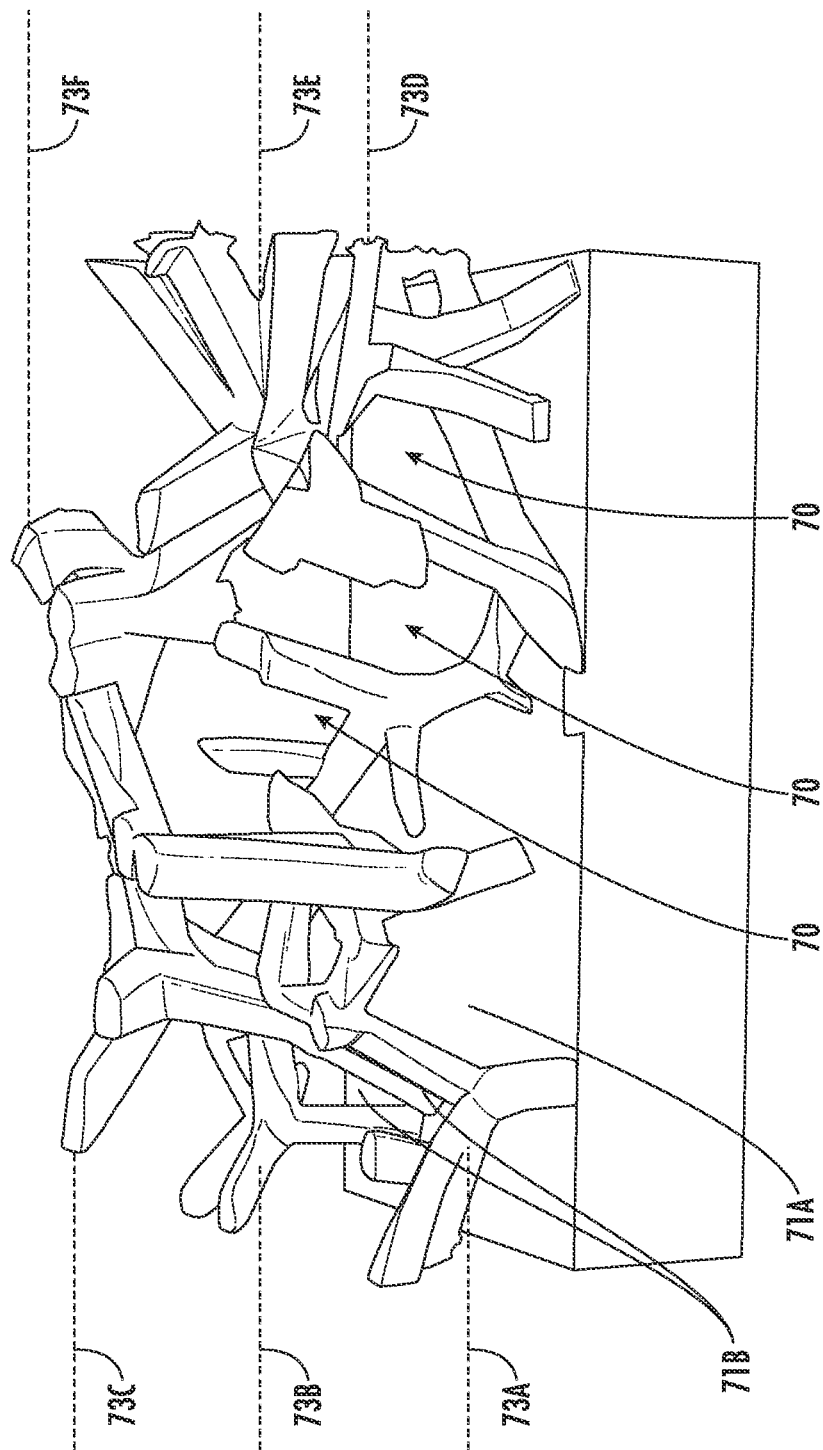
FIG. 13 is a back view of the portion of the surface of the interbody spacer shown in FIG. 11.
Figure 14:
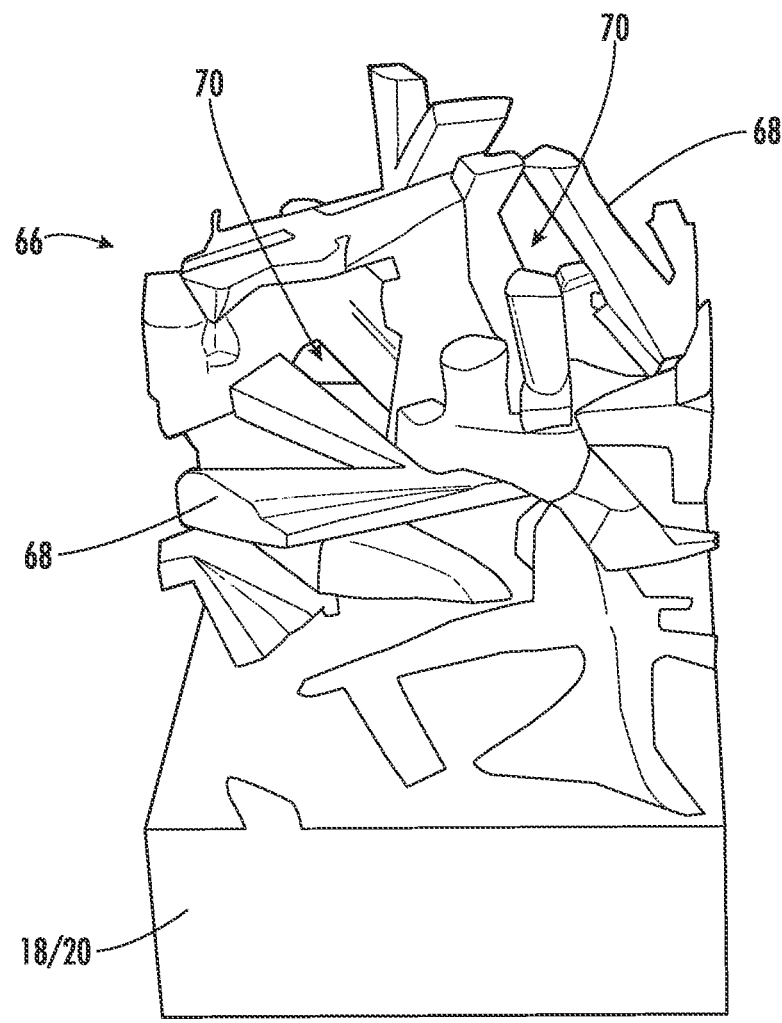
FIG. 14 is a side view of the portion of the surface of the interbody spacer shown in FIG. 11.

The pore 70A may be formed from independent linear segments 68, one of which forms a linear segment bridge 66D with a linear segment 68 in close proximity. Additionally, or alternatively, the pore 70 may be formed or defined by a plurality of clumped together linear segments 68, see for example pore 70B, FIG. 12. Pore 70B is formed by a plurality of multi-branched segments 68 interconnecting, which form lattices or combine together at different levels, i.e. at different heights or planes relative to the surface 69. The dashed lines 73A, 73B, 73C, 73D, 73E, and 73F shown in FIG. 13 represent the different heights or planes described above. As such, within the pore 70, multiple, independent pores 70 can be formed as well, each at different heights, planes, or combinations thereof.

In a preferred embodiment, the surface projection pattern or matrix 66 is at least 1 mm thick and within the lattice structure two distinct layers. The upper layer of the surface projection pattern or matrix 66 comprises of a layer of pore sizes ranging from about 600 to 1000 microns. The lower layer of the surface projection pattern or matrix 66 comprises of a layer of pore sizes ranging from about 50 to 5000 microns.

Figure 18:
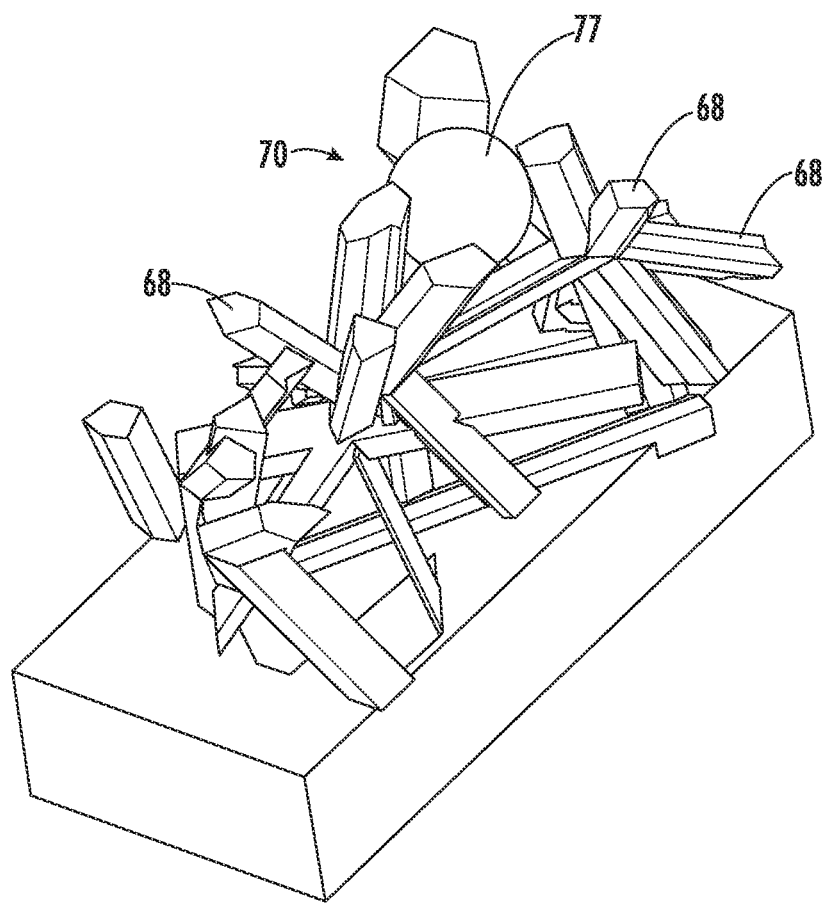
FIG. 18 illustrates a sphere having at least a diameter of about 600 to about 1000 microns placed within a pore.
Figure 19:
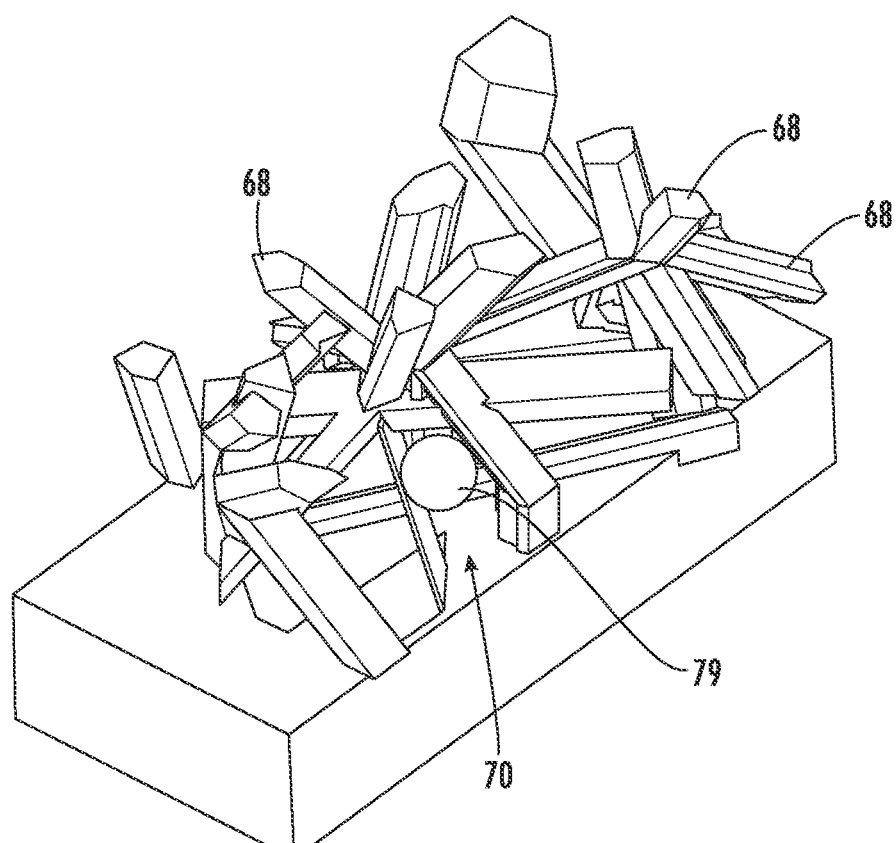
FIG. 19 illustrates a sphere having at least a diameter of about 50 to about 500 microns placed within a pore.

As used herein, a "pore size" may be defined by the size of an object, preferably a sphere, which fits within the pore, i.e. within the opening or slot formed by the linear segments 68 that define the pore. Accordingly, the pore sizes of the upper layer are sized to fit an object, such as a sphere 77, see FIG. 18, of between, about 600 to about 1000 microns. The pore sizes of the lower layer are sized to fit an object, such as a sphere 79, see FIG. 19, of between, about 50 to about 500 microns. The upper layer and the lower layer may have some variance, having some pore sizes larger than defined. Accordingly, the upper layer or the lower layer may also be defined by having pores sizes of which at least about 1%—about 99% of the pores are between about 600 to about 1000 microns (upper layer) or between about 50 to about 500 microns (lower layer), including at least between about 90—about 99%, at least between about 80—about 89%, at least between about 70—about 79%, at least between about—60—about 69%, at least between about 50—about 59%, at least between about 40—about 49%, at least between about 30—about 39%, at least between about 20—about 29%, at least between about 10—about 19%, or at least about between 1—about 9%.

As used herein the term "about" defines a value of 10-20% above or below the stated value.

As illustrated in FIGS. 1-10, surface projection pattern or matrix 66 preferably covers all of the first or upper wall, or surface 18, and all of the second or lower wall, or surface 20. However, the first or upper wall, or surface 18, and all of the second or lower wall, or surface 20, may be designed with surface projection pattern or matrix 66 covering less. In addition, while two opposing side walls 22 and 24 are shown without surface projection pattern or matrix 66, such feature can be applied thereto as well.

Figure 16:
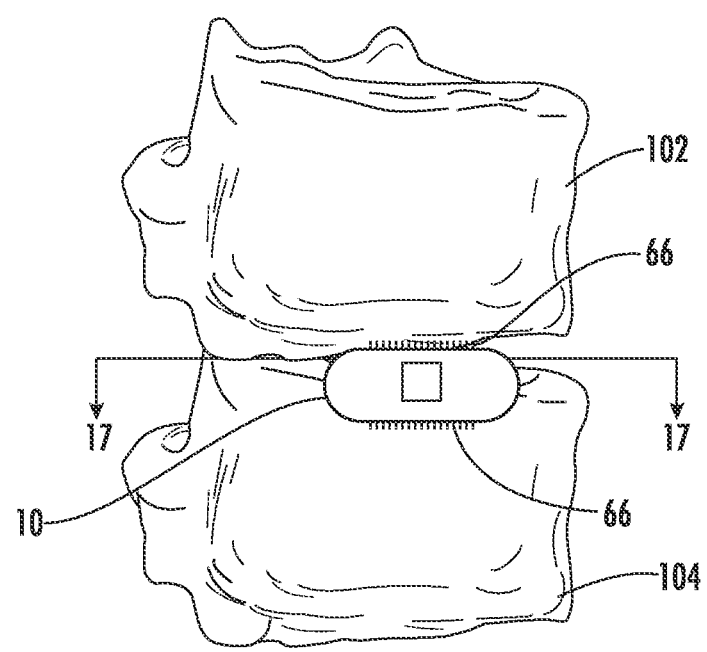
FIG. 16 is a perspective view of a spinal section, illustrated with an interbody spacer in the disc space.
Figure 17:
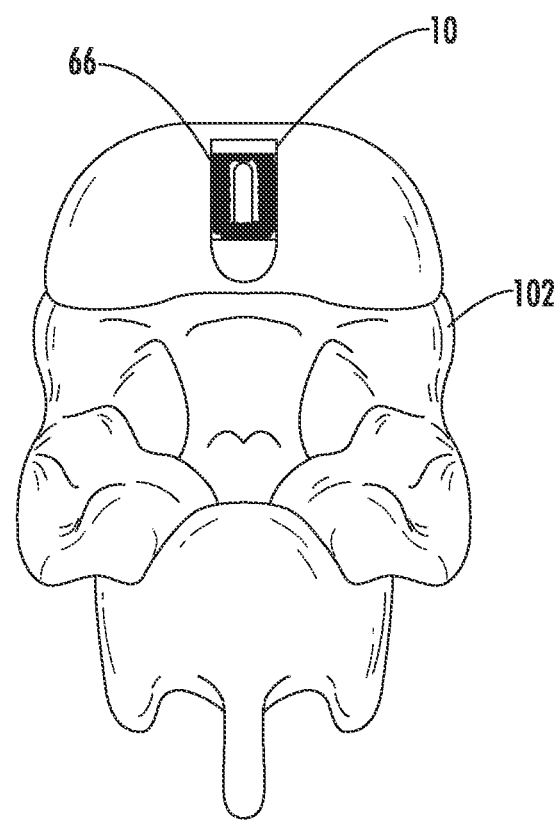
FIG. 17 is a section view taken along lines 17-17 of FIG. 16.

FIGS. 16 and 17 illustrate the interbody spacer 10 in use associated with a spinal procedure. The interbody spacer 10 is shown inserted between two adjacent vertebrae 102 and 104, with surface projection pattern or matrix 66 aligned to contact the vertebrae 102 or 104.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical implant having a unique surface pattern comprising:

an elongated intervertebral spacer body having a distal end, a proximal end, an upper wall comprising an upper surface, a lower wall comprising a lower surface, opposing side walls, and an internal cavity configured to hold bone growth material, said upper wall, said lower wall, and said opposing side walls each comprising an opening formed therethrough, said openings each sized and shaped to expose the internal cavity, said distal end comprising a plurality of angled surfaces tapering to a flat, distal-most end surface, said proximal end comprising a plurality of angled surfaces tapering to a flat, proximal-most end surface, the flat proximal-most end surface comprising an opening forming a recessed insertion tool cavity configured to receive and threadably engage with a portion of an insertion tool, and said upper surface or said lower surface having a surface scaffold defined by a plurality of surface projections arranged to define a plurality of pores therebetween, the surface scaffold including two distinct scaffold layers, one positioned adjacent to the other, comprising an upper layer and a lower layer, wherein some of said surface projections comprise irregularly shaped linear segments having at least one irregular flat surface along one or more sides thereof, an irregular cross section, appearing crystalline, and arranged as an irregular lattice structure with some of the linear segments arranged to intersect other linear segments at random points while some of the linear segments do not intersect other linear segments, wherein spaces between the intersections define some of the pores, the pores each having a unique irregular shape with respect to adjacent pores, wherein some of said surface projections comprise irregularly shaped linear segments having a plurality of flat surfaces separated by a curvature or twist extending along a longitudinal axis of the respective linear segment, and wherein some of said surface projections comprise a single linear segment which branches off into one or more branches, said one or more branches further branching off into sub-branches, some of said sub-branches intersecting with other linear segments in the surface scaffold.

2. The surgical implant having a unique surface pattern according to claim 1, wherein the pores of the upper layer are sized in a range and the pores of the lower layer are sized in a range, the pore size range of the upper layer being different from the pore size range of the lower layer.

3. The surgical implant having a unique surface pattern according to claim 2, wherein said pore size of the upper layer ranges from about 600 to 1000 microns.

4. The surgical implant having a unique surface pattern according to claim 2, wherein said pore size of the lower layer ranges from about 50 to 5000 microns.

5. The surgical implant having a unique surface pattern according to claim 1, wherein at least one of the pores is surrounded by linear segments so that it is disconnected from adjacent pores, defining a closed pore.

6. The surgical implant having a unique surface pattern according to claim 1, wherein the pores comprises both independent and irregularly shaped pores formed at different heights or planes with respect to the upper and lower surfaces of the spacer body.

7. The surgical implant having a unique surface pattern according to claim 1, wherein said spacer body is made from titanium.

\* \* \* \* \*